United States Patent [19]

Sealfon

[11] Patent Number: 4,604,994

[45] Date of Patent: Aug. 12, 1986

[54] IMPLANTABLE MEDICAL PROSTHESIS FOR OBVIATING MALE IMPOTENCY

[75] Inventor: Andrew I. Sealfon, Port Washington, N.Y.

[73] Assignee: Repro-Med Systems, Inc., Middletown, N.Y.

[21] Appl. No.: 747,938

[22] Filed: Jun. 24, 1985

[51] Int. Cl.[4] ............................................. A61F 5/00
[52] U.S. Cl. ..................................................... 128/79
[58] Field of Search ......................... 128/79, DIG. 25; 604/135, 132, 213, 891

[56] References Cited

U.S. PATENT DOCUMENTS

| | | | |
|---|---|---|---|
| 3,954,102 | 5/1976 | Buuck | 128/79 |
| 4,127,118 | 11/1978 | Latorre | 128/79 |
| 4,224,934 | 9/1980 | Scott et al. | 128/79 |
| 4,342,308 | 8/1982 | Trick | 128/79 |
| 4,383,525 | 5/1983 | Scott et al. | 128/79 |
| 4,399,812 | 8/1983 | Whitehead | 128/79 |
| 4,404,968 | 9/1983 | Evans, Sr. | 128/79 |

Primary Examiner—Gene Mancene
Assistant Examiner—Cary E. Stone
Attorney, Agent, or Firm—Bauer & Amer

[57] ABSTRACT

A manually compressible reservoir, such as a rubber bulb is provided in which a liquid medication is maintained and from which an outlet conduit extends to a selected body part. The prosthesis includes a piston for storing separately from the reservoir a predetermined dose of medication and which piston is responsive to the manual compression of the reservoir to discharge the predetermined dose and on release to automatically cause the medication to flow from the reservoir to restore a predetermined dose so that repeated operation and delivery of medication is possible.

8 Claims, 6 Drawing Figures

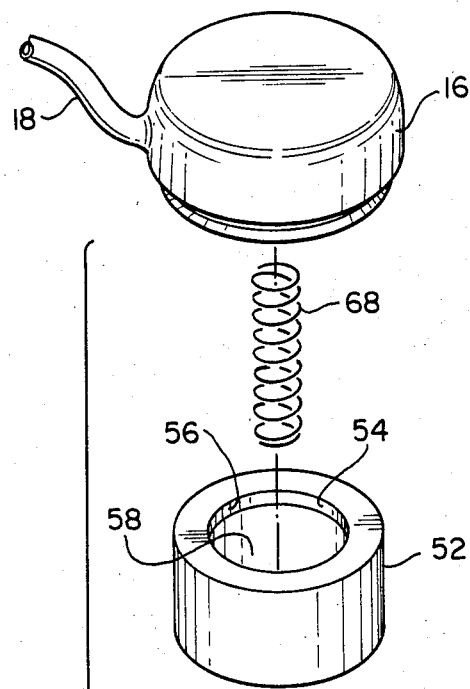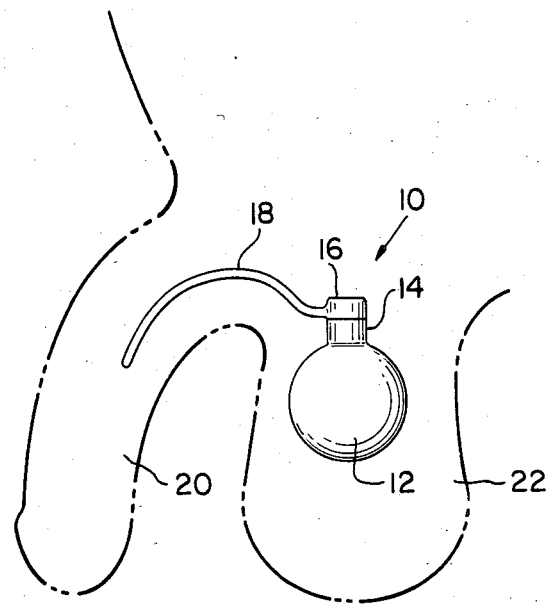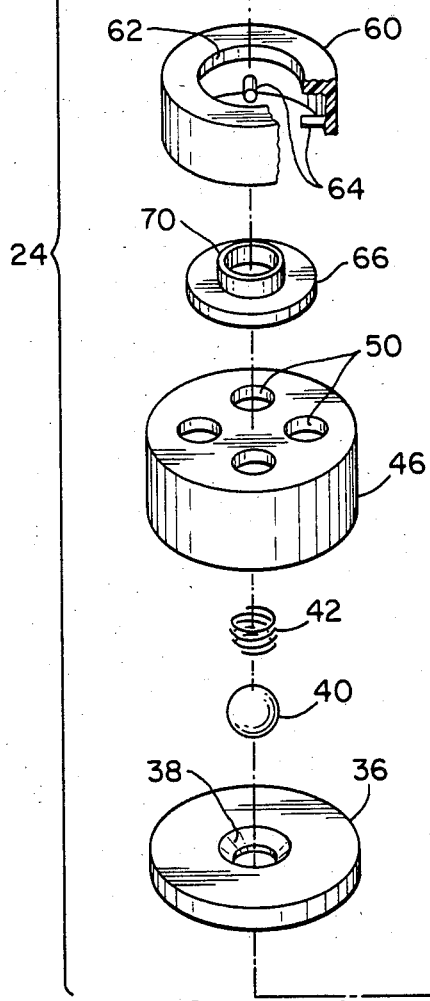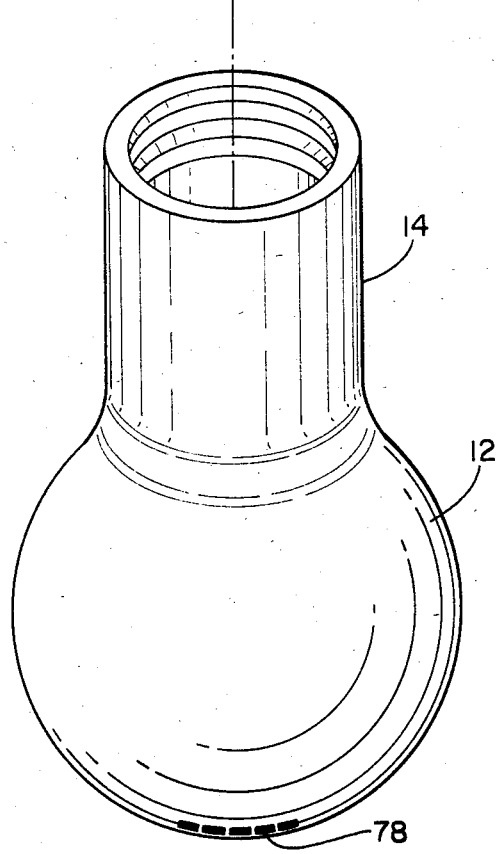
FIG.1
FIG.2

IMPLANTABLE MEDICAL PROSTHESIS FOR OBVIATING MALE IMPOTENCY

BACKGROUND OF THE INVENTION

The present invention relates to an implantable medical prosthesis for delivering precise doses of medication to selected tissues and in particular, to an implantable prosthesis for supplying medication to the body to stimulate a natural penile erection.

Therapeutic success has been widely reported, in the last decade or so, for the injection directly into the penis of certain nerve blocking agents which permit normal body functions to stimulate dilation of the blood vessels in the penis, thus causing the arterial pressure by which an erection is created.

A broad discussion of this subject and of the chemical compositions effecting penile erection is to be found in U.S. Pat. No. 4,127,118 in which use was made of a dual barrel hypodermic device by which the selected vasodilator is injected from the exterior of the penis directly into the corpora cavernosa.

While improvement in the chemical agents have been made as reported on in more recent medical journals, little improvement, if any, has been made in the apparatus by which the agents are injected into the penis. The use of an external hypodermic device has several disadvantages, particularly amongst which is the pain caused to the user each time an injection is made. Another disadvantage lies in the absence of surety that the necessary specific dose is delivered in precise manner directly to the corpora canervosa so that a natural erection can be had. Still another disadvantage lies in the fact that the injection must be made sufficiently prior to the initiation of coitus so as to avoid interruption or to avoid any psychological reluctance in the presence of the female partner. It is not infrequent that the injection is made so early that its effect has dissipated before successful coitus.

It is the object of the present invention to overcome the disadvantages found in the prior art devices and to provide means by which precise doses of vasodilators can be easily and effectively delivered to the corpora cavernosa in a timely and on demand manner.

It is a specific object of the present invention to provide an implantable prosthesis from which precise doses can be delivered to the penis without repeated injection.

It is another object to provide an implantable prosthesis capable of holding and delivering repeated doses of chemical agents over an indefinite time period, and which is capable of heing refilled periodically.

It is another object of the present invention to provide an implantable prosthesis in the form of a dosimeter capable of delivering precise doses or calculated amounts of chemical agents by hand manipulation by the user alone.

These objects and advantages together with numerous other advantages will become apparant from the following disclosure of the present invention.

SUMMARY OF THE INVENTION

According to the present invention, an implantable prosthesis is provided specifically for use in stimulating penile erection, although it can be employed readily to deliver medication to varous other body parts or organs. The prothesis comprises a manually compressible reservoir, such as a rubber bulb, in which a liquid medication is maintained and from which an outlet conduit extends to the selected body part. The prothesis includes means for storing separately from the reservoir a predetermined dose of medication and which means is responsive to the manual compression of the reservoir to discharge the predetermined dose and on release to automatically cause the medication to flow from the reservoir to restore a predetermined dose so that repeated operation and delivery of medication is possible.

The reservoir is refillable from outside the body, by simple hypodermic syringe. However, it is preferred that the dose be calculated as a small fraction of the medication held in the reservoir so that the reservoir can hold sufficient medication to enable the delivery of a large number of doses before the reservoir needs refilling. The reservoir bulb is provided with at least a small section, which is self sealing so that repeated puncturing will not destroy the integrity of the reservoir.

Preferably, the means for storing and delivering the predetermined dose comprises a cylinder/piston pump like dosimeter in which the piston normally divides the cylinder into a precise fixed volume storage chamber in which medication is held, and an antechamber communicating with and receiving fluid from the reservoir. The piston is provided with a valve disc, which is closed, on squeezing of the reservoir, causing the piston to move through the fixed volume chamber to expel the precise dose and on release of the reservoir opens allowing the piston to reverse its direction and permitted passage of fluid from the antechamber into the fixed volume chamber. Thus, the dosimeter is constantly filled with fluid, avoiding any air pockets which might be harmful to the patient or to the smooth operation of the prothesis.

To insure a continuous body of fluid in the dosimeter a unidirectional valve is provided sealing the reservoir from the dosimeter in the non-operative or rest position.

Full details of the present invention are set forth in the following description and illustrated in the accompanying drawings.

BRIEF DESCRIPTION OF THE DRAWINGS

In the drawings:

FIG. 1 is a schematic view showing the prosthesis embodying the present invention implanted within the body;

FIG. 2 is an exploded isometric view of the prosthesis;

DESCRIPTION OF THE INVENTION

Figure 3A:
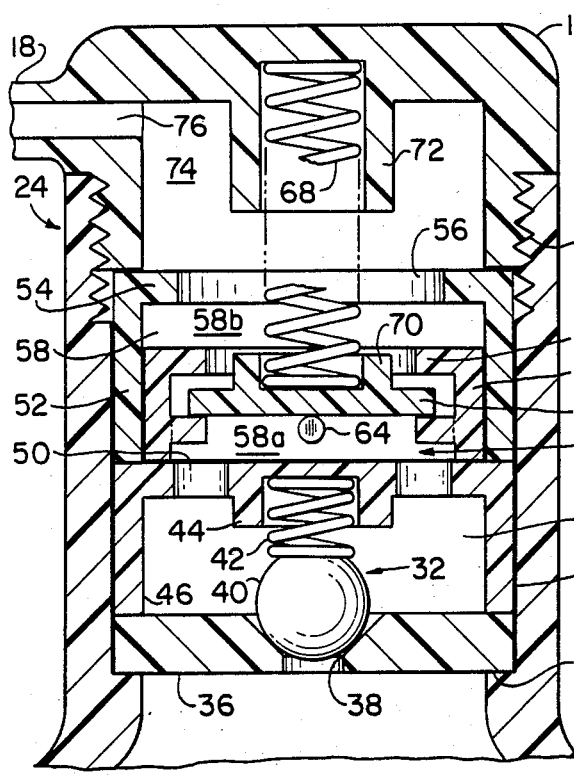
FIGS. 3A through 3D are sectional views of the dosimeter device, employed in the prosthesis, showing in sequence its operational cycle.

The present invention, as shown in FIG. 1, comprises a prosthesis generally depicted by the numeral 10, consisting of a resiliently flexible bulb 12 serving as a reservoir, to the neck 14 of which is attached a screw cap 16 from which a flexible conduit 18 extends into the penis 20. The entire device 10 as seen, is implanted within the scrotum 22 with the conduit 18 extending into the penis where it is implanted within both or a selected one of the corpora cavernosa (not shown).

To insure proper dispensing and dosing, the prosthesis is provided with a dosimeter, generally depicted by the numeral 24, located below the cap 16 within the neck 14 of the bulb. The neck 14 is relatively hard, as compared with the remainder of the bulb, and is provided as seen in FIG. 3, in its interior with a radial shoulder 26, a smooth interior wall 28, and an internal thread 30 at its free end into which the cap 16, having an exterior thread is screwed.

As seen in FIGS. 3A–3D, the dosimeter 24 is divided into a unidirectional check valve assembly 32 and a pump 34 for discharging a fixed volume of fluid to the conduit 18. The check valve assembly 32 comprises an annular wall 36 inserted into the neck 14 of the bulb 12 to seat against the radial shoulder 26. The wall 36 has a central conically shaped hole 38 in which a ball 40 is seated, biased by a spring 42. The spring 42 is itself seated within a central boss 44 formed in an inverted cup-shaped spacer 46, placed over the wall 36 and pressing against the wall 36 so as to define an enclosed space 48 for receiving fluid passing through the conical hole 38. Surrounding the boss 44 of the spacer 46 are a plurality of holes 50 allowing flow of fluid out of the space 48.

The pump assembly 34 comprises an exterior sleeve-like housing 52 extending from the top of the spacer 46 to the cap 16 which cap presses the housing 52 against spacer 46, on being screwed within the neck 14. The end opposite the spacer 46 is provided with a radially inwardly directed flange 54, defining an enlarged central opening 56. Between the flange 54 and the spacer 46 the housing 52 defines a chamber 58, in which is housed a movable piston 60, dividing the chamber 58 into a lower antechamber 58a communicating with the reservoir through the check valve 32, and an upper pump chamber 58b communicating with the conduit 18.

The piston 60, which like the housing is a cylinder having a radially inwardly directed flange 62. The piston 60 is slidable in fluid tight contact with the wall of the housing 52 between a lower position seen in FIG. 3A, wherein its lower edge abuts against the spacer 46 to an upper position seen in FIG. 3C, where the housing flange 54 forms a stop for the piston.

A plurality of radially inwardly directed pins 64 are spaced below the flange 62, the pins 64 being integrally formed and circumferentially spaced from each other to permit introduction between them of a valve disc 66. The pins 64 are also spaced axially from the flange 62 so as to permit the valve disc 66 to move freely between the pins and flange to open the hole and close the hole in the piston. The disc 66 is sufficiently rigid so as to be unbendable under the pressure exerted by the fluid in the prosthesis and to provide a closed seal in combination with the piston flange 62 when in abutment against the flange.

The disc 66 is normally biased away from the flange 62 by a spring 68 which is seated at one end in a boss 70 formed on the upper face of the disc 66 and at its other end in a boss 72 formed on the lower face of the cap 16.

The central opening 56 opens from the pump assembly into a space 74 formed in the cap 16 from which extends a radially directed outlet port 76 to which is connected the conduit 18 leading to the corpora cavernosa.

The prosthesis is preferably formed of durable plastic material inert to body fluids and particularly to the chemical constituents of the vasodilator used. The thickness of the bulb wall is relatively thin so as to be responsive to squeezing by the patient so as to discharge the fluid into the corpora cavernosa but of sufficient memory retention so as to automatically resume its original shape and maintain its shape against unintentional forces exerted on the scrotum. A portion of the bulb 12 is formed of self-sealing puncture material, 78 (FIG. 1) allowing it to be periodically filled by hypodermic syringe. The size of the bulb and the amount of vasodilator needed for any given dose may be calculated such that even a small bulb capable of being implanted in the scrotum would be sufficient to hold a supply of vasodilator for several months thereby perhaps requiring refilling, at most twice a year.

At the time the prosthesis is implanted, the bulb 12 is filled with the desired fluid and simultaneously the dosimeter, as generally defined is primed with fluid so that all the cavities within the spacer 46 and the housing 52 below the flange 54 are filled with the fluid. Once the device is thus prepared, the dosimeter takes the positions shown in FIG. 3A wherein the ball 40 seats in hole 38 and check valve assembly 32 is closed off from the fluid in the bulb. The pressure of the remaining fluid in the dosimeter combined with the bias of the spring 42 maintains the check valve closed.

Figure 3B:
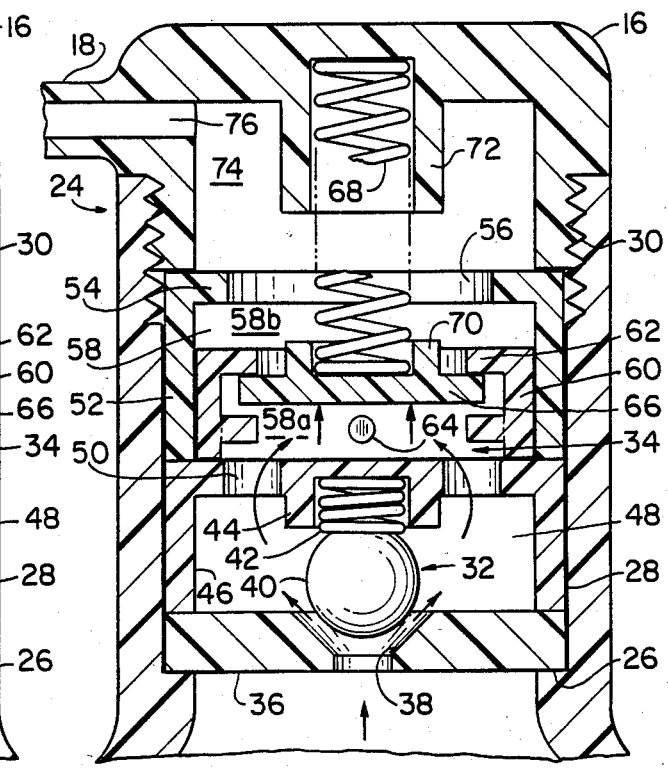

When the patient desires an erection, he merely squeezes the bulb 12. The fluid from the bulb forces itself through the hole 38, lifting the ball 40 from its seat and causing the fluid in the entry space 48 to increase in pressure. The fluid pressure passes through holes 50 increasing likewise the pressure in the ante pump chamber 58a causing the disc valve to move and seat against the flange 62 of the piston 60. The piston 60 is thereafter subjected to increasing pressure from the ante pump chamber 58a and the piston 60 is itself raised against the bias of the spring 68. This reduces the volume of the upper chamber 58b causing the fluid previously found in the upper pump chamber 58b to pass through the central opening 56 into the cap and out the outlet port 76. Simultaneously fluid continues to flow from the bulb 12, as seen in FIG. 3B into the check valve space 48, and the antechamber 58a which is now increased size.

Figure 3C:
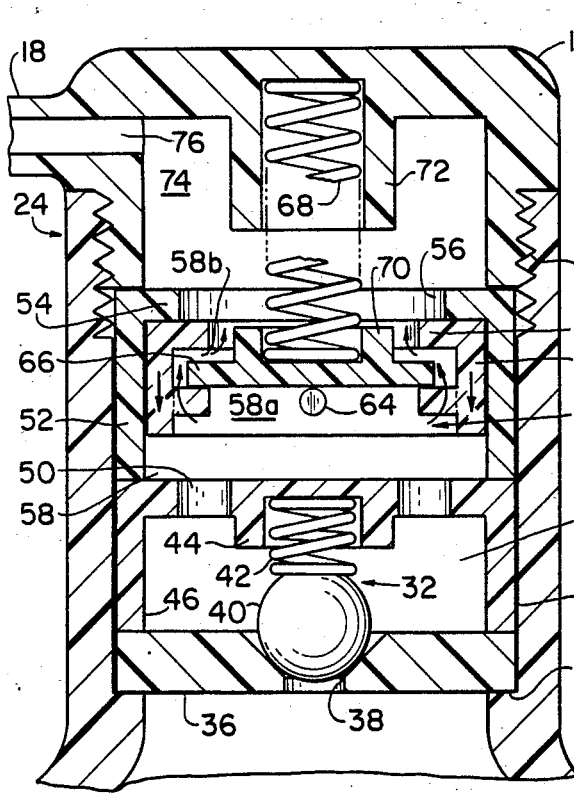
Figure 3D:
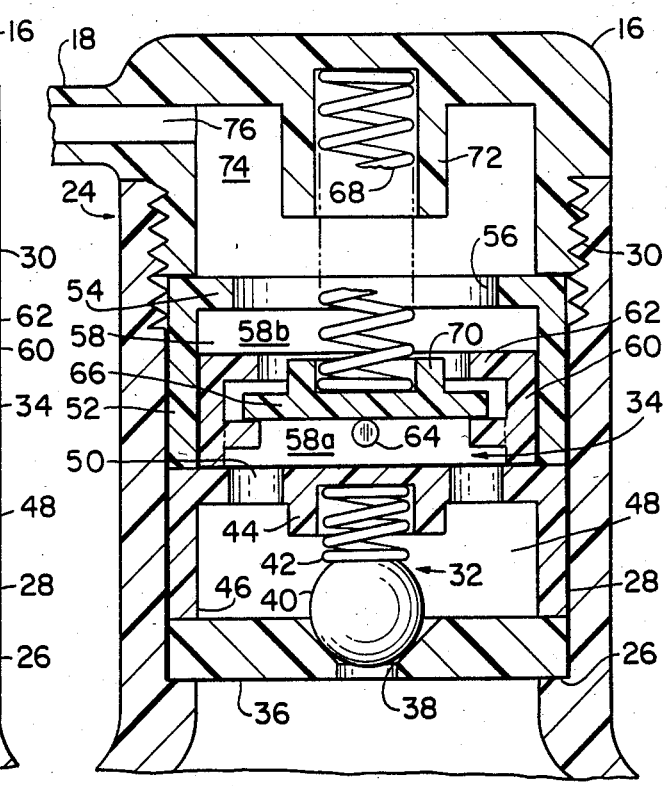

Once the piston 60 reaches its uppermost positon, the piston flange 62 and valve disc 66 seal the central opening 56 and no further fluid can pass through to the outlet port 58 and thus fluid flow from the bulb through the dosimeter is arrested. This arrestation is sensed by the patient who thus releases the bulb. As a result of which the ball 40 drops immediately closing the check valve 32. This causes a decrease in pressure on the valve disc 66 which then falls onto the pins 64, opening passage for fluid, from the antechamber 58a, to pass through the piston into the upper pump chamber 58b. Consequently, together with the bias of the spring 68, the reduction in pressure allows the piston, and the piston disc to descend as seen in FIG. 3C. As the piston descends, the upper pump chamber 58b enlarges becoming filled with fluid once again. When the dosimeter returns to its initial or rest position once again, as seen in FIG. 3A, the upper pump chamber 58b is completely full containing exactly the same fixed volume of fluid as it had during the initial and/or preceding cycle of operation. The check valve 32 is closed and the internal spaces and chambers are again prepared and readied for the next cycle of operation. It is obvious that only the amount of fluid contained in the upper chamber had passed into the corpora cavernosa.

It will be obvious from the foregoing that the several objects and advantages enumerated earlier have been obtained by the present invention in its various embodiments. Several embodiments and changes have been suggested herein, others will be obvious to those skilled in this art. It is intended, therefore, that the present disclosure be taken as illustrative only and not limiting of the present invention.

What is claimed is:

1. An implantable medical prosthesis for the demand delivery of medication comprising a manually compressible reservoir for maintaining a quanity of fluid medication within the body and having an outlet from said reservoir for directing said fluid medication to a selected part of the body, including means for normally storing a predetermined dose of said fluid medication in advance of said outlet in readiness for discharge to the body, said means being responsive to compression of said reservoir to discharge said stored predetermine dose and responsive to the subsequent release of compression to be automatically supplied with an amount of fluid from said reservoir equal to the amount of discharged dose to restore a predetermined dose of fluid medication for succeeding discharge.

2. The prosthesis according to claim 1 wherein said predetermined dose of medication is a fraction of the fluid medication initially provided to said reservoir whereby repeated cycle operation of said means effects repeated discharge of medication.

3. The prosthesis according to claim 1 wherein said reservoir is refillable by syringe injection from outside the body.

4. The prosthesis according to claim 1 wherein said means for storing and discharging said predetermined dose comprises a cylinder/piston dosimeter in which the piston normally divides the cylinder into a pump chamber of fixed volume and an antechamber communicating with and receiving medication from the reservoir, said piston having valve means which on compression of said reservoir is caused to close enabling the piston to move responsive to the increased pressure of the fluid in the antechamber though the pump chamber to expel the medication therefrom, and on cessation of compression to open permitting the piston to return to normal position while fluid from the antechamber passes through the valve means into a storage chamber.

5. The prosthesis according to claim 4 including a check valve interposed between said antechamber and said reservoir to permit unidirectional flow of fluid from said reservoir to said antechamber.

6. The prosthesis according to claim 5 wherein said check valve comprises a ball valve resilently biased to maintain a closed position when said reservoir is not compressed.

7. The prosthesis according to any one of claims 4-6 wherein said piston is provided with a central aperture and said valve means comprises a disc adapted to close and open said aperture, said disc being normally biased on its open position and being subject to the flow of fluid from said reservoir to close.

8. A prosthesis for implantation in the scrotum for delivering medication on demand to the penis, comprising a compressible bulb providing a reservoir for a supply of fluid medication having an outlet conduit extending into the corpora cavernosa of the penis, said prosthesis including a dosimeter interposed between said reservoir and said conduit, said dosimeter comprising a cylinder and a piston movable in said cylinder between a rest position and a discharge position, said piston in the rest position dividing said cylinder into a storage chamber of predetermined volume communicating with the outlet conduit, and a antechamber communicating with and receiving fluid from said reservoir, said piston having a unidirection valve means closable in response to an increase in pressure in the antechamber and openable on a decrease of pressure therein, said piston being movable into the discharge position by compression of said bulb creating a flow of fluid into said antechamber, said piston being subsequently returned into the rest position on release of the compression, said valve means simultaneously opening allowing refilling of the storage chamber with fluid from the antechamber on return of the piston to said rest position.

* * * * *